Figure 1:
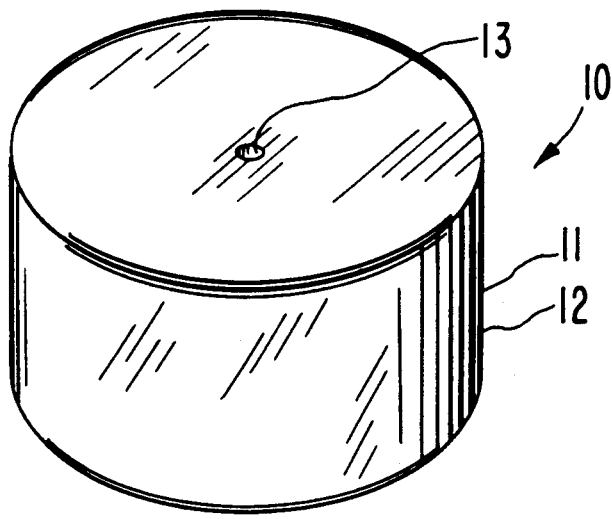

United States Patent [19]
Edgren et al.

[11] Patent Number: 5,057,321
[45] Date of Patent: Oct. 15, 1991

[54] DOSAGE FORM COMPRISING DRUG AND MALTODEXTRIN

[75] Inventors: David E. Edgren, El Granada; Gurdish K. Bhatti, Fremont; Howard A. Carpenter, Palo Alto, all of Calif.

[73] Assignee: ALZA Corporation, Palo Alto, Calif.

[21] Appl. No.: 538,046

[22] Filed: Jun. 13, 1990

[51] Int. Cl.⁵ ............................................. A61K 9/24
[52] U.S. Cl. .................... 424/413; 424/439; 604/892.1
[58] Field of Search ............... 424/473, 499, 498, 439; 604/892.1

[56] References Cited
U.S. PATENT DOCUMENTS

| | | | |
|---|---|---|---|
| 3,845,770 | 11/1974 | Theeuwes et al. | 128/260 |
| 3,916,899 | 11/1975 | Theeuwes et al. | 128/260 |
| 4,327,725 | 5/1982 | Cortese et al. | 128/260 |
| 4,822,597 | 4/1989 | Faust | 424/48 |

Primary Examiner—Thurman K. Page
Assistant Examiner—D. Gabrielle Phelan
Attorney, Agent, or Firm—Paul L. Sabatine; Edward L. Mandell; Steven F. Stone

[57] ABSTRACT

A dosage form is disclosed comprising a drug and a maltodextrin polymer for administering to a patient a drug in need of therapy.

7 Claims, 3 Drawing Sheets

DOSAGE FORM COMPRISING DRUG AND MALTODEXTRIN

DESCRIPTION OF TECHNICAL FIELD

This invention pertains to an improvement in a dosage form. The dosage form comprises a wall that surrounds a compartment comprising a drug, wherein the improvement comprises a maltodextrin in the compartment that cooperated with the dosage form for delivering the drug from the compartment, while concomitantly permitting the drug to substantially maintain both its chemical integrity and therapeutic activity.

DESCRIPTION OF BACKGROUND ART

Dosage forms for delivering a drug to a biological environment of use are known to the prior art in U.S. Pat. Nos. 3,845,770 and 3,916,899, issued to the patentees Felix Theeuwes and Takeru Higuchi. The dosage forms disclosed in these patents comprise a wall that surrounds an internal compartment containing the drug. The wall is permeable to the passage of an external fluid and it is substantially impermeable to the passage of drug. There is at lease one passageway through the wall for delivering the drug from the dosage form. These dosage forms release the drug by fluid being imbibed through the wall into the compartment at a rate determined by the permeability of the wall and the osmotic pressure gradient across the wall to produce an aqueous solution containing drug that is dispensed through the passageway from the dosage form. These dosage forms are extraordinarily effective for delivering an agent that is soluble in fluid imbibed into the dosage form that exhibits and osmotic pressure gradient across the wall against an external fluid.

A pioneer advancement in dosage form invention was presented to the drug delivery arts by Richard Cortese and Felix Theeuwes in U.S. Pat. No. 4,327,725. The invention disclosed and claimed in this patent pertained to enhancing the delivery kinetics of the dosage form for delivering drugs with various degrees of solubility in aqueous fluids that are difficult to deliver, by manufacturing the dosage form comprising a hydrogel. The hydrogel in the presence of fluid imbibed into the dosage form, swells and moves from a rested state to an expanded state. The force generated by the expansion of the hydrogel is applied against the drug thereby pushing the beneficial drug through the passageway from the dosage form.

The dosage forms provided by the prior art operate successfully for their use, and they can deliver numerous drugs. Now, it has been found that some hydrogels used in these dosage forms often exhibit an unwanted effect on the drug, that causes it to lose its chemical integrity and therapeutic activity. That is, the drug may decompose and consequently the intact drug is not available for delivery from the dosage form.

In light of the above presentation, it will be appreciated by those versed in the dispensing art to which this invention pertains, that a pressing need exists for a rate controlled dosage form that can deliver a drug intact to a patient in need of therapy. It will be appreciated further by those versed in the delivery arts, that if a dosage form is provided comprising a hydrogel that can deliver a drug substantially-free of the unwanted effects of the prior art, such a dosage form would have a positive value and it also would represent both an improvement and an advancement in the dispensing arts.

DISCLOSURE OF OBJECTS OF THE INVENTION

Accordingly, it is an immediate object of this invention to provide a dosage form for the controlled delivery of a drug, by providing a dosage form that represents a further improvement and advancement in the delivery arts.

Another object of this invention is to provide a novel and useful dosage form manufactured as an osmotic delivery device, the use of which dosage form requires intervention only for initiation of its use for producing a therapeutic result.

Another object of this invention is to provide a dosage form that can deliver a substantial amount of a drug rate controlled by the dosage form throughout the day, with once, and sometimes twice daily, dosing by the dosage form.

Another object of this invention is to provide a dosage form comprising a compartment comprising a drug and an expandable hydrophilic maltodextrin that is substantially-free of exhibiting an unwanted effect on the drug.

Another object of the present invention is to provide a dosage form for delivering a drug wherein the drug and a maltodextrin are in the dosage form, with the maltodextrin substantially-free from exerting an adverse or deteriorating effect on the drug.

Another object of this invention is to provide a dosage form comprising a pharmaceutically acceptable maltodextrin that is chemically inert, safe for administering to a warm-blooded animal, and imparts stability to a drug in a dosage form.

Another object of the invention is to provide a dosage form having a compartment comprising a drug that is insoluble to very soluble in an aqueous fluid, and an expandable maltodextrin driving member, which maltodextrin operates by expanding to diminish the space occupied by the drug, thereby delivering the drug from the dosage form at a controlled rate over time.

Another object of the invention is to provide an osmotic dosage form having a compartment housing a layer of a composition comprising a drug, and an adjacent layer of a composition comprising an expandable maltodextrin, which latter layer continuously increases its volume while correspondingly decreasing the volume initially occupied by the drug composition during the operation of the dosage form.

Another object of the present invention is to provide a dosage form manufactured as an osmotic dosage form that can deliver a drug while simultaneously substantially reducing and/or substantially eliminating the unwanted influences of the gastrointestinal tract environment of use.

Another object of the present invention is to provide a dosage form designed and manufactured as an osmotic device containing a drug and a maltodextrin, which drug is delivered in a dose amount for producing the desired therapeutic effect, and which device delivers substantially a full complement of the drug, thereby avoiding the need for a drug overage in the dosage form.

Another object of the invention is to provide a dosage form that provides instant drug therapy and prolonged drug therapy using a maltodextrin.

Other objects, features and advantages of the invention will be more apparent to those versed in the dispensing arts from the following detailed specification, taken in conjunction with the drawings and the accompanying claims.

BRIEF DISCLOSURE OF THE DRAWING FIGURES

Figure 2:
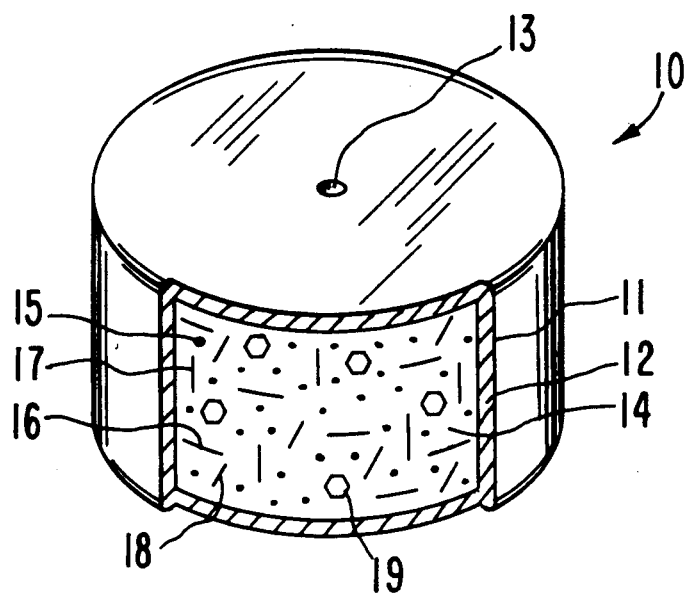
Figure 3:
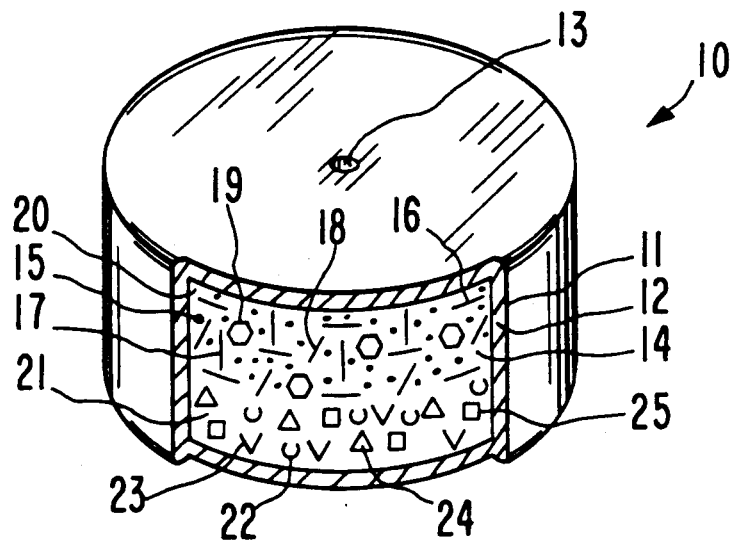
Figure 4:
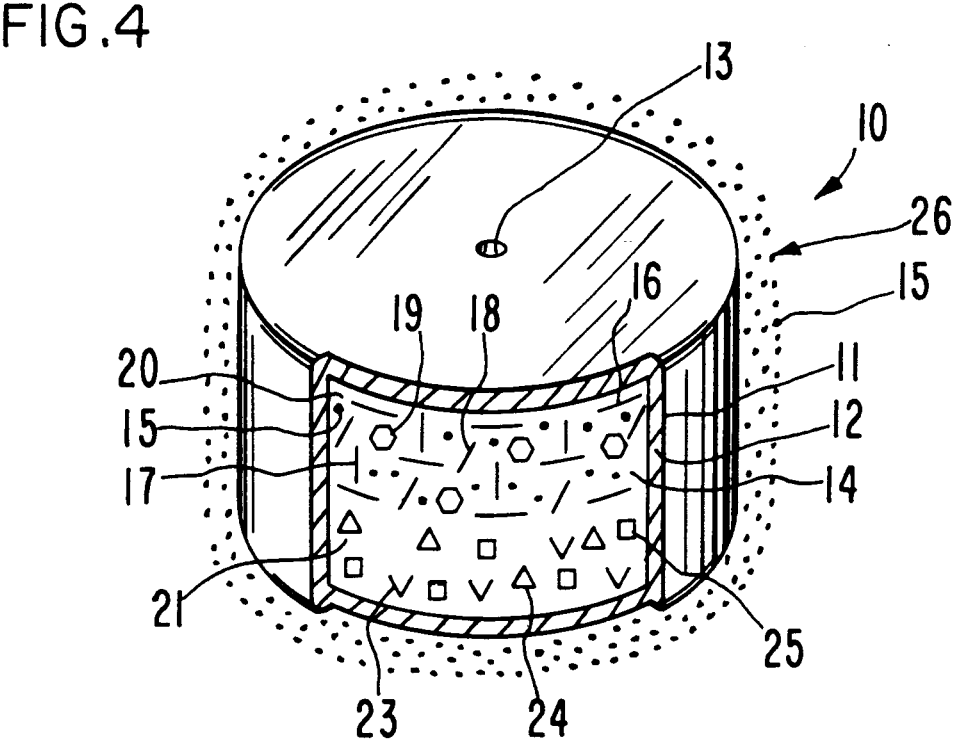
Figure 5:
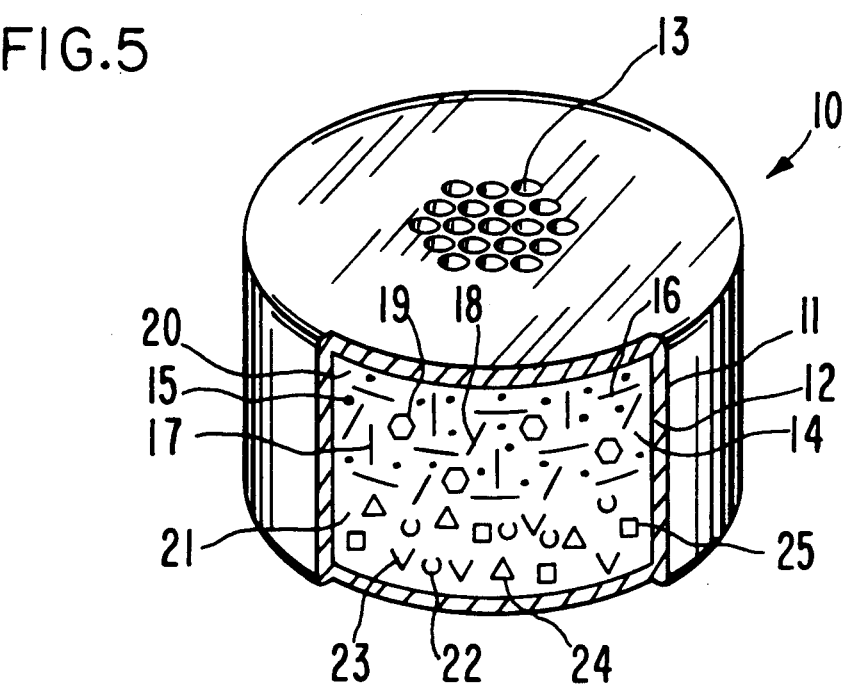
Figure 6:
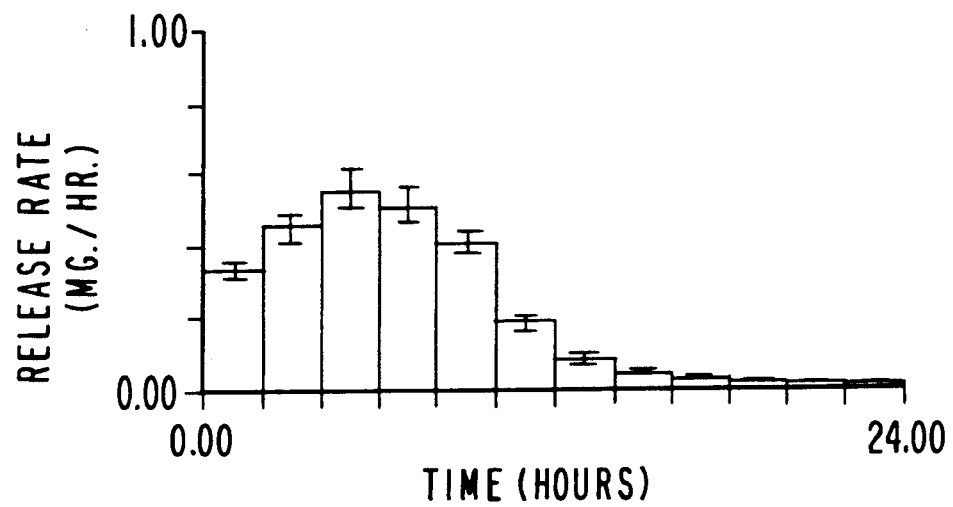
Figure 7:
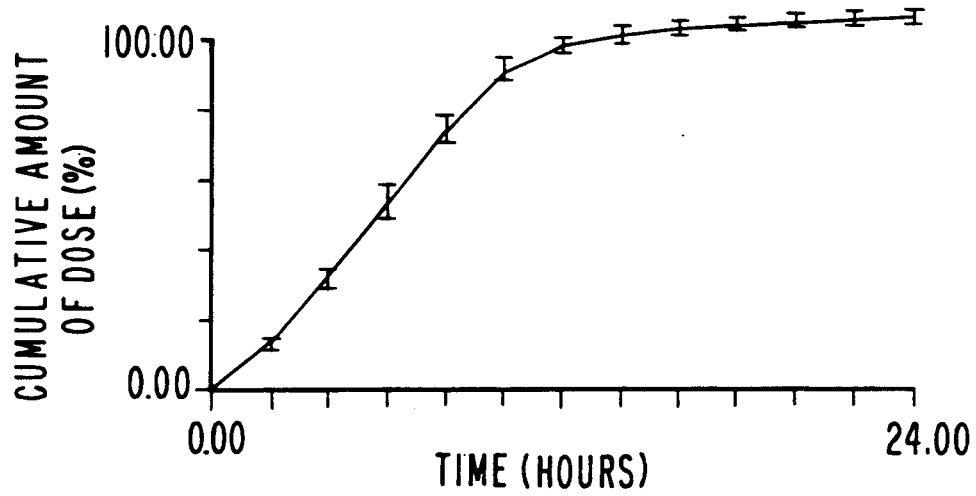

In the drawing figures, which are not drawn to scale, but are set forth to illustrate various embodiments of the invention, the drawing figures are as follows:

Drawing FIG. 1 is a view of a dosage form, designed, shaped and adapted for administering orally a drug in the gastrointestinal of a human in need of therapy;

Drawing FIG. 2 is an opened view of the dosage form of drawing FIG. 1 for illustrating the internal structure and ingredients of a dosage form;

Drawing FIG. 3 is an opened view of the dosage form of drawing FIG. 1 for illustrating the internal structure comprising a first drug composition and a second maltodextrin composition;

Drawing FIG. 4 is an opened view of the dosage form of drawing FIG. 1, which drawing FIG. 4 depicts the structure of the dosage form comprising a first drug composition, a second maltodextrin composition, and an instant drug released on the outside of the dosage form;

Drawing FIG. 5 is an opened view of the dosage form of drawing FIG. 1, which drawing FIG. 5 depicts a multiporous releasing member for releasing drug from the dosage form;

Drawing FIG. 6 is a graph that illustrates the amount of drug release per hour from a dosage form; and Drawing FIG. 7 is a graph that illustrates the amount of drug release in a cumulative amount over a prolonged time of 24 hours.

In the drawing figures, and in the specification, like parts in related drawing figures are identified by like numbers. The terms appearing earlier in the specification and in the description of the drawing figures, as well as embodiments thereof, are further described elsewhere in the specification.

DETAILED DISCLOSURE OF THE DRAWING FIGURES

Turning now to the drawing figures in detail, which drawing figures are an example of the dosage form provided by this invention, and which example is not to be construed as limiting, one example of the dosage form is illustrated in drawing FIG. 1, and designed by the numeral 10. In drawing FIG. 1, dosage form 10 comprises a body member 11 comprising wall 12, which wall surrounds an enclosed internal compartment, not seen in drawing FIG. 1. Dosage form 10 comprises at least one exit means 13 in wall 12, which exit means connects the exterior environment of use with the interior of dosage form 10.

In drawing FIG. 2, dosage form 10 is manufactured as an osmotic device, and it is seen in opened view. In drawing FIG. 2, dosage form 10 comprises body 11, a wall 12, which wall surrounds and defines an internal compartment 14. Wall 12 comprises at least one exit means 13 that connects compartment 14 with the exterior of dosage form 10. Dosage form 10 can comprise more than one exit means, as presented later in the specification.

Wall 12 of dosage form 10, comprises totally, or in at least a part, a composition that is permeable to the passage of an exterior fluid present in the environment of use. Wall 12 is substantially impermeable to the passage of a drug and to other optional ingredients that may be present in compartment 14. The semipermeable wall 12 is substantially inert, that is, wall 12 maintains its physical and chemical integrity during the dispensing of a therapeutic drug form dosage from dosage form 10. Wall 12, in a presently preferred embodiment is formed totally or in at least a part of a member selected from the group consisting of a cellulose ether, cellulose ester, and cellulose ester-ether. These cellulosic polymers have a degree of substitution, D.S., on the anhydroglucose unit, from greater than 0 up to 3 inclusive. By degree of substitution is meant the average number of hydroxyl groups originally present on the anhydroglucose unit comprising the cellulose polymer that are replaced by a substituting group. Representative materials include a member selected from the group consisting of cellulose acylate, cellulose diacylate, cellulose triacylate, cellulose acetate, cellulose diacetate, cellulose triacetate, mono, di and tricellulose, alkanylates, mono, di and tricellulose aroylates, and the like. Exemplary polymers include cellulose acetate having a D.S. up to 1 and an acetyl content up to 21%; cellulose acetate having an acetyl content of 32 to 39.8%; cellulose acetate having a D.S. of 1 to 2 and an acetyl content of 21 to 35%; cellulose acetate having a D.S. of 2 to 3 and an acetyl content of 35 to 44.8%, and the like. More specific cellulosic polymers include cellulose propionate having a D.S. 1.8 and a propyl content of 39.2 to 45% and a hydroxyl content of 2.8 to 5.4%; cellulose acetate butyrate having a D.S. of 1.8, an acetyl content of 13 to 15% and a butyryl content of 34 to 39%; cellulose acetate butyrate having an acetyl content of 2 to 29%, a butyryl content of 17 to 53% and a hydroxyl content of 0.5 to 4.7%; cellulose triacylates having a D.S. of 2.9 to 3 such as cellulose triacetate, cellulose trivalerate, cellulose trilaurate, cellulose tripalmitate, cellulose trisuccinate, and cellulose trioctanoate; cellulose diacylates having a D.S. of 2.2 to 2.6% such as cellulose disuccinate, cellulose dipalmitate, cellulose dioctanoate, cellulose dipentanoate, co-esters of cellulose such as cellulose acetate butyrate and cellulose acetate propionate, and the like.

Additional semipermeable polymers include acetaldehyde dimethyl cellulose acetate, cellulose acetate ethyl carbamate, cellulose acetate methyl carbamate, cellulose acetate dimethyl aminoacetate, semipermeable polyamides; semipermeable polyurethanes; semipermeable sulfonated polystyrenes; semipermeable cross-linked selectively permeable polymers formed by the coprecipitation of a polyanion and a polycation as disclosed in U.S. Pat. Nos. 3,173,876; 3,276,586; 3,541,005; 3,541,006; and 3,546,142; semipermeable polymers as disclosed by Loeb and Sourirajan in U.S. Pat. No. 3,133,132; semipermeable lightly cross-linked polystyrene derivatives; semipermeable cross-linked poly(sodium styrene sulfonate); and semipermeable cross-linked poly(vinylbenzyltrimethyl ammonium chloride). The polymers are known to the art in U.S. Pat. Nos. 3,845,770; 3,916,899; and 4,160,020; and in Handbook of CommonPolymers by Scott, J. R. and Roff, W. J., 1971, published by CRC Press, Cleveland, Ohio.

In another embodiment, wall 12 comprises additionally from 0 weight percent, "wt %," to 30 weight percent of a member selected from the group consisting of a cellulose ether selected from the group consisting of a hydroxypropylcellulose and a hydroxypropylmethylcellulose, and from 0 weight percent to 30 weight percent of a polyethylene glycol. The total weight of all components comprising wall 12 is equal to 100 weight percent.

Internal compartment 14 comprises a drug 15, represented by dots, which drug is present in a therapeutically effective amount comprising 10 nanogram to 650 mg for producing a therapeutic effect. Compartment 14 also comprises from 0 weight percent to 35 weight percent of a hydroxypropylmethylcellulose, identified by dashes 16 comprising a 9,000 to 300,000 molecular weight; from 0 weight percent to 75 weight percent of hydroxypropylcellulose represented by vertical lines 17 and comprising 10,000 to 100,000 molecular weight, from 0 weight percent to 75 weight percent of a polyvinyl pyrrolidone represented by slanted lines 18 comprising a 20,000 to 275,000 molecular weight; from 5 weight percent to 75 weight percent of a maltodextrin polymer composition comprising the formula $(C_6 H_{12} O_5)_n H_2O$ wherein n is 3 to 6,140 and the maltodextrin polymer comprises a 500 to 1,000,000 number average molecular weight represented by hexagon 19, and from 0 to 3 weight percent of a lubricant such as magnesium stearate, or stearic acid; with the total weight of all ingredients equal to 100 weight percent.

Drawing FIG. 3, seen in opened view, depicts a dosage form 10 comprising in compartment 14 a first composition 20 and a second composition 21. The first composition 20 and the second composition 21 initially are in laminar arrangement and they cooperate with each other and with dosage form 10 for effectively delivering drug 15 from dosage form 10. First composition 20 also comprises from 0 weight percent to 25 weight percent of a hydroxypropylmethylcellulose 16 comprising a 9,000 to 300,000 average molecular weight; from 0 weight percent to a 50 weight percent of a hydroxypropylcellulose 17 comprising a 10,000 to 300,000 molecular weight; from 0 weight percent to 50 weight percent of a polyvinyl pyrrolidone 18 comprising a 20,000 to 275,000 molecular weight; from 5 to 95 l wt % of maltodextrin polymer 19 of the formula $(C_6 H_{12} O_5)_n$ $H_2O$ wherein n is 3 to 61,400 and the maltodextrin polymer comprises a 500 to 10,000,000 number average molecular weight. The maltodextrin can comprise a broad range of average degree of polymerization and molecular weight such as a degree of polymerization, "DP", of 3.1 and a molecular weight, "mol. wt", of 500; a DP of 4.5 and a mol. wt of 720; a DP of 5.6 and a mol. wt of 900; a maltodextrin polymer having a DP of 7.4 and a mol. wt of 1200; a DP of 11.1 and a mol. wt of 1800; a DP of 22.1 and a mol. wt of 3600; and the like. The maltodextrin can be formulated into first composition 20 by manufacturing processes including wet, dry or fluidizing processes. The maltodextrins are pharmaceutically acceptable, they are compatible with other ingredients in second composition 21, they are free-flowing powders in their dry state and on imbibing an aqueous fluid they form an expanding, osmotic plastic paste at 75 to 100% relative humidity. The maltodextrin polymers are commercially available from the Grain Processing Corporation of Muscatine, Iowa. First composition 20 may optionally comprise from 0 wt % to 3 wt % of a lubricant such as a member selected from the group consisting of stearic acid, magnesium stearate, zinc stearate, zinc oleate, zinc palmitate, calcium stearate, micronized polyethylene glycol, finely divided teflon and hydrogenated castor oil; and from 0 to 3 wt % of a surfactant selected from the group consisting of nonionic, anionic, cationic, amphoteric surfactants, micelles surfactants, olefin surfactants, quaternary surfactants, and the like, with the total amount of all components in the first composition equal to 100 wt %.

Second composition 21 comprises from 0 to 40 weight percent of an osmotically effective compound, which are also known as osmotically effective solutes and osmagents, and they are represented in drawing FIG. 3 by half-circles 22. The osmotic solutes 22 are homogeneously or heterogeneously blended with other second composition 21 forming ingredients for imbibing an external fluid through wall 12 into composition 21. Osmotically effective solutes used for the purpose of this invention comprise a member selected from the group consisting of magnesium sulfate, magnesium chloride, potassium sulfate, sodium sulfate, lithium sulfate, mannitol, urea, inositol, magnesium succinate, sodium chloride, potassium chloride, raffinose, sucrose, glucose, lactose, sorbitol and the like. Osmotic solutes and procedures for measuring their osmotic pressure using a Model 320B, Vapor Pressure Osmometer, manufactured by Hewlett-Packard Co., Avondale, PA., are disclosed by Wong et al in U.S. Pat. No. 4,765,989.

Second composition 21 comprises from 5 weight percent to 95 weight percent of a hydrogel identified by V 23. The hydrophilic composition suitable for forming second composition 21 are swellable, hydrophilic polymers. The presently preferred materials useful for forming second composition 21 comprise hydrogels that exhibit the ability to swell and expand in the presence of water and retain a significant fraction of water within the hydrogel structure. The hydrogels can be noncross-linked, or they can be lightly crossed linked. The polymer hydrogels swell or expand to a very high degree in the presence of aqueous type fluids, usually exhibiting a 2 to 60 volume increase. This expansion against first composition 20 results in the drug being delivered through exit passageway 13. Hydrophilic polymeric compositions useful for the present purpose include poly(hydroxyalkyl methacrylate); poly(N-vinyl-2-pyrrolidone); anionic hydrogels; cationic hydrogels; polyelectrolyte hydrogel complexes; poly(-vinyl alcohol) cross-linked with glyoxal, formaldehyde or glutaraldehyde; copolymers produced by forming a dispersion of finely divided copolymer of maleic anhydride with styrene, ethylene, propylene, butylene or isobutylene; polymeric N-vinyl lactams; carboxypolymers available as Carbopol ® polymer; Cyanamer ® polyacrylamides cross-linked with inden-maleic anhydride; Good-Rite ®polyacrylic acid; Aqua Keeps ®acrylate polymer; diester cross-linked polyglucan; polyethylene oxide; copolymers of N-vinyl lactam with N-vinyl piperidione; Water Lock ®starch-graft-poly(iodine acylate-co-acrylamide); sodium carboxymethylcellulose; and the like. The degree of expansion is calculated by subtracting the weight of the dry hydrogel from the weight of the aqueous swollen hydrogel divided by the weight of the dry hydrogel times 100. The hydrogel polymers are disclosed in U.S. Pat. No. 4,327,725 issued to Cortese and Theeuwes, and in U.S. Pat. No. 4,612,008 issued to Wong, Barclay, Deters and Theeuwes. Second composition 21 comprises from 0 to 25 wt % of a hydroxypropylcellulose identified by triangle 24, and from 0 to 35 wt % hydroxypropylmethylcellulose identified by squares 25. Second composition 21 optionally comprises from 0 wt % to 3 wt % of a coloring agent such as ferric oxide and optionally from 0 to 3 wt % of all ingredients present in second composition 21 is equal to 100 wt %.

Dosage form 10, as seen in drawing FIG. 4, is manufactured as an osmotic device comprising an external drug coat 26 on the exterior or semipermeable wall 12. Coat 26 is a composition comprising 1 mg to 100 mg of drug 15, represented by the dots, and an aqueous soluble carrier such as a low molecular weight, 5,000 to 200,000 grams per mole hydroxypropylcellulose, or a low molecular weight, 9,000 to 22,000 grams per mole hydroxypropylmethylcellulose. The coat optionally contains a plasticizer such as polyethylene glycol. Drug coat 26 provides instant therapy as coat 26 dissolves or undergoes dissolution or disintegration in the presence of aqueous and biological fluids and concurrently therewith delivers a drug to a drug receptor. Drug coat 26 provides immediate drug delivery, thereby essentially overcoming the time required for a drug to be delivered from internal compartment 14. A start-up time is needed for imbibing fluid through wall 12 for dosage form 10 to osmotically and hydrodynamically pump drug from dosage form IO, through exit means 13.

Drawing FIG. 5 depicts, in opened section, another drug delivery device provided by the invention. In drawing FIG. 5, exit means 13 comprises a microporous inlay that spreads the drug as it is osmotically released from the dosage form 10. The expression, "exit means" 13, as used herein, comprises means and methods suitable for the metered release of a beneficial drug from compartment 15 of dosage form IO. The means 13 includes at lease one passageway, orifice, or the like, through wall for communicating with in compartment 14. The expression, at least one passageway, includes aperture, orifice, bore, pore, porous element through which the drug can be pumped, diffuse, travel or migrate, hollow fiber, capillary tube, porous overlay, porous insert, microporous member, and the like. The expressions also includes a material that erodes or is leached from wall 12 in the fluid environment of use to produce at least one passageway in dosage form 10. Representative material suitable for forming at least one passageway, or a multiplicity of passageways, include an erodible poly(glycolic) acid or poly(lactic) acid member in the wall; a gelatinous filament, poly(vinyl alcohol); leachable materials such as fluid removable pore forming polysaccharides, salts, or oxides, and the like. A passageway or a plurality of passageways can be formed by leaching a material such as sorbitol, sucrose, lactose, fructose, or the like, from the wall. The passageway can have any shape such as round, triangular, square, elliptical, and the like, for assisting in the metered release of drug from dosage form 10. Dosage form 10 can be constructed with one or more passageways in spaced apart relations on one or more than a single surface of a dosage form. Passageways and equipment for forming passages are disclosed in U.S. Pat. Nos. 3,845,770 and 3,916,899 by Theeuwes and Higuchi; in U.S. Pat. No. 4,063,064 by Saunders et al; and in U.S. Pat. No. 4,088,864 by Theeuwes et al. Passageways formed by leaching to provide a drug-releasing pore of controlled osmotic release rate are disclosed in U.S. Pat. No. 4,200,098 by Ayer et al; and in U.S. Pat. No. 4,285,987 by Ayer et al.

The expression, "drug 15", as used for the purpose of this invention comprises a member selected from the group consisting of IO aids chemotherapeutic drugs, adrenal cortical steroid inhibitors, adrenal corticosteroids, alcohol abuse reduction preparations, allergens, allergy relief products, amino acid preparations, analgesics, anesthetics, anorectal, antacids, antibacterials, antiseptics, antibiotics, anticholinergic drug inhibitors, anticoagulant antagonist, anticoagulants, antidepressants, antiduretus, antidose, antiglucomatous, antihistamines, antiinflammatory, antimetabolites, antineoplastics, antioxidants, antiparasites, antipyretus, antispasmodirs, anticholinergus, appetite suppressants, antiarthritics, asthma, biologicals, bone metabolism regulators, bowel evacuants, bronchial dilators, cardiovascular, cerebral metabolic enhancers, cholinesterase inhibitors, cold drugs, contraceptives, convulsion medications, cortuosteroids, cough preparations, decongestants, dental preparations, dermatologicals, detoxifying agents, diabetes drugs, diagnostics, diarrhea medications, dietary supplements, diuretics, dopamine receptor agonist, duodenal ulcer adherent complex, electrolytes, enuresis, enzymes, ergot preparations, fertility agents, fibrinolytic agents, flatulence relief, fluoride preparations, foods, fungal agents, glactokinectics, galactorrhea inhibitors, gall stone dissolution agents, gastric acid secretion inhibitors, gastrointestinal motility factor, gonadotropin inhibitors, hair growth stimulants, hematinics, hemostatics, herpes treatment drugs, histamine receptor antagonists, hyperammonia reduction agents, hyperglycemia drugs, hypnotics, hypocalcemia management drugs, hypolipdimus, laxatives, menstrual agents, migraine drugs, minerals, motion sickness remedies, microlytics, muscle relaxant antagonist, muscle relaxants, mydriatics, narcotic antagonists, nasal drugs, nausea medications, neuroleptics, osteoporosis drugs, oxytocics, parasympatholytic, parasympathommetics, Parkinson drugs, prostagladins, protozal drugs, prurtis medications, psychostimulants, psychotic medications, respiratory stimulants, sedatives, sleep aids, smoking cessation aids, sympatholytics, sympathomimetics, throat lozenges drugs, thrombolytins, thyroid, preparations, tranquilizers, tremor preparations, tuberculosis preparations, uricosuric agents, urinary IO tract agents, uterine contractants, uterine relaxants, vaginal drugs, vertigo agents, viral therapy, vitamins, and x-ray contrast agents. The dose unit amount of a drug in the delivery system is 1 mg to 750 mg. The generic drugs are known in *Physician's Desk References,* 44th Edition, 1990, published by Medical Economics Company, Inc., Oradell, N.J.

DESCRIPTION OF METHODS OF PERFORMING THE INVENTION

Wall 12 of osmotic dosage form 10 can be formed in one technique using the air suspension procedure. This procedure consists in suspending and tumbling the compressed laminate in a current of air and wall forming composition until a wall is applied to the drug forming compartment. The air suspensions procedure is well-suited for independently forming the wall. The air suspension procedure is described in U.S. Pat. No. 2,799,241; *J. Am. Pharm. Assoc.,* Vol. 48, pages 451 to 459, 1959; and ibid. Vol. 49, pages 82 to 84, 1960. Osmotic dosage forms can also be coated with a wall-forming composition in a Wurster ®air suspension coater, using acetone-water cosolvent, 90:10, wt:wt, using 2.5 to 4 wt % solids. The Aeromatic ®air suspension coater using a methylene dichloride methanol cosolvent, 87:13, v:v, also can be used for applying the wall. Other wall forming techniques such as pan coating can be used for providing the dosage form. In the pan coating system, wall forming compositions are deposited by successive spraying of the composition on the bilayered compartment, accompanying by tumbling in a rotating pan. A pan coater is used to produce thicker walls. A larger volume of methanol can be used in a cosolvent to produce a thinner wall. Finally, the wall coated compartments are dried in a forced air oven at 30° C. to 50° C. for a week to free the dosage form of solvent. Generally, the walls formed by these techniques have a thickness of 2 to 20 mils with a presently preferred thickness of 4 to 10 mils.

Dosage form IO of the invention is manufactured by standard manufacturing techniques. For example, in one manufacturer the beneficial drug and other ingredients comprising the first layer facing the exit means are blended and pressed into a solid layer. The drug and other ingredients can be blended also with a solvent and mixed into a solid or semisolid formed by conventional methods such as ball-milling, calendering, stirring or rollmilling and then pressed into a preselected shape. The layer possesses dimensions that correspond to the internal dimensions of the area the layer is to occupy in the dosage form and it also possesses dimensions corresponding to the second layer for forming a contacting arrangement therewith. Next, the osmopolymer, or hydrogel layer is placed in contact with the drug layer. The layering of the drug layer and the osmopolymer layer can be fabricated by conventional press-layering techniques. Finally, the two layer compartment forming members are surrounded and coated with an outer wall. A passageway is laser drilled through the wall to contact the drug layer, with the dosage form optically oriented automatically by the laser equipment for forming the passageway on the preselected surface.

In another manufacture, the dosage form is manufactured by the wet granulation technique. In the wet granulation technique, the drug and the ingredients comprising the first layer are blended using an organic or inorganic solvent, such as isopropyl alcohol-methylene dichloride 80/20 v/v as the granulation fluid. Other granulating fluid such as water or denatured alcohol 100% can be used for this purpose. The ingredients forming the first layer are individually passed through a 40 mesh screen and then thoroughly blended in a mixer. Next, other ingredients comprising the first layer are dissolved in a portion of the granulation fluid, such as the cosolvent described above. Then, the latter prepared wet blend is slowly added to the drug blend with continual mixing in the blender. The granulating fluid is added until a wet blend is produced, which wet mass then is forced through a 20 mesh screen onto oven trays. The blend is dried for 18 to 24 hours at 30° C. to 50° C. The dry granules are sized then with a 20 mesh screen. Next, a lubricant is passed through an 80 mesh screen and added to the dry screened granule blend. The granulation is put into milling jars and mixed on a jar mill for 10 to 15 minutes. The composition is pressed into layers for example in a Manesty ®press layer press. The second layer is pressed in a similar manner.

Another manufacturing process that can be used for providing the compartment-forming composition comprises blending the powdered ingredients in a fluid bed granulator. After the powdered ingredients are dry blended in the granulator, a granulating fluid, for example poly(vinyl-pyrrolidone) in water, is sprayed onto the powders. The coated powders are then dried in a granulator. This process granulates all the ingredients present therein while adding the granulating fluid. After the granules are dried, a lubricant such as stearic acid or magnesium stearate is blended as above into the mixture. The granules are pressed then in the manner described above.

The osmotic device of this invention is manufactured in another embodiment by mixing a drug with composition forming ingredients and pressing the composition into a solid lamina possessing dimensions that correspond to the internal dimensions of the compartment space adjacent to a passageways. In another embodiment the drug and other first composition forming ingredients and a solvent are mixed into a solid, or a semisolid, by conventional methods such as ballmilling, calendering, stirring or rollmilling, and then pressed into a preselected lamina forming shape. Next, a lamina of a composition comprising an osmopolymer and an optional osmagent are placed in contact with the lamina comprising the drug, and the two lamina comprising the laminate are surrounded with a semipermeable wall. The lamination of the first drug composition and the second osmopolymer optional osmagent composition can be accomplished by using a conventional two-layer tablet press technique. The wall can be applied by molding, spraying or dipping the pressed shapes into IO wall forming materials. Another and presently preferred technique that can be used for applying the wall is the air suspension coating procedure. This procedure consists in suspending the tumbling the two layered laminate in current of air until the wall forming composition surrounds the laminate. The air suspension procedure is described in U.S. Pat. No. 2,799,241; *J. Am. Pharm. Assoc.*, Vol. 48, pp 451–459 (1979); and, ibid, Vol. 49, pp 82–84 (1960). Other standard manufacturing procedures are described in *Modern Plastics Encyclopedia*, Vol. 46, pp 62–70 (1969); and in *Pharmaceutical Science*, by Remington, 14th Ed., pp 1626–1979, (1970), published by Mack Publishing Co., Easton, PA.

Exemplary solvents suitable for manufacturing the wall, the laminates and laminae include inert inorganic and organic solvents that do not adversely harm the materials and the final wall of the final laminated wall. The solvents broadly include members selected from the group consisting of aqueous solvents, alcohols, ketones, esters, ethers, aliphatic hydrocarbons, halogenated solvents, cycloaliphatics, aromatics, heterocyclic solvents and mixtures thereof. Typical solvents include acetone, diacetone alcohol, methanol, ethanol, isopropyl alcohol, butyl alcohol, methyl acetate, ethyl acetate, isopropyl acetate, n-butyl acetate, methyl isobutyl ketone, methyl propyl ketone, n-hexane, n-heptane, ethylene glycol monoethyl ether, ethylene glycol monethylacetate, methylene dichloride, ethylene dichloride, propylene dichloride, carbon chloroform, nitrethane, nitropropane, tetrachloroethane, ethyl ether, isopropyl ether, cyclohexane, cyclo-octane, toluene, naphtha, 1,4-dioxane, tetrahydrofuran, diglyme, aqueous and nonaqueous mixtures thereof, such as acetone and water, acetone and methanol, acetone and ethyl alcohol, methylene dichloride and methanol, and ethylene dichloride and methanol.

DETAILED DISCLOSURE EXAMPLES OF THE INVENTION

The following examples are merely illustrative of the present invention and they should not be considered as limiting the scope of the invention in any way as these example and other equivalents thereof will become apparent to those versed in the art in the light of the present disclosure, the drawings and the accompanying claims.

EXAMPLE 1

A dosage form adapted, designed and shaped as an osmotic drug delivery device is manufactured as follows: first, all the ingredients are pre-sieved through a #40 mesh screen, and 50 g of bromocriptine mesylate is then blended with 40 g of maleic acid in a Hobert ®blender for 15 minutes. Then, add 200 g of hydroxypropylcellulose to the blend and continue mixing for 10 to 12 minutes. Next, blend 700 g of maltodextrin exhibiting a degree of polymerization of 11.1 and a molecular weight of 1800 with the hydroxypropylcellulose, bromocriptine mesylate, maleic acid blend and blend all the ingredients for 20 minutes. Next, add 10 g of polyethylene glycol 30 castor oil, a surfactant, to 100 ml of anhydrous ethyl alcohol and mix until dissolved; and then, slowly add this alcohol solution to the mixing dry blend in the blender, to produce a damp mass. Next, mix for 10 minutes and pass the damp mass through a 20 mesh screen, to produce a damp granulation. Allow the granulation to air dry at ambient conditions over night. The dry mass then is passed through a 20 mesh screen to produce granules.

Next, 700 ml of distilled water is added to a stainless steel mixing vessel, its mixer started, followed by adding 63 g of hydroxypropylcellulose to the water with mixing continuously to produce a solution. The remaining dry ingredients are screened through a 40 mesh screen. Then, 550 g of sodium carboxymethylcellulose, 290 g of sodium chloride, 77 g of hydroxypropylcellulose and optionally 20 g of ferric oxide are blended into a homogeneous blend. The just prepared blend is added to a fluid bed granulator machine, and the above solution is sprayed onto the screened blend. After all the granulating solution has been sprayed onto the screened blend, the granulation is dried in the fluidizing air for about 10 minutes. The granulation is removed from the column and passed through a 20 mesh screen. Next, 0.5 wt % of stearic acid and 0.2 wt % of silicon dioxide previously passed through an 80 mesh screen is added to the granulation, and the ingredients are blended for 4 minutes to yield the second push composition.

The first composition and the second composition are arranged into bilayer cores by compressing 125 mg of the first composition and 85 mg of the second composition together under a force of about 2 tons. The bilayer cores were coated with a coating solution comprising a binary solvent of methylene chloride and methanol comprising cellulose triacetate and polyethylene glycol. The bilayers were coated in an Aeromatic ®coater with 500 g of coating composition until a uniform semipermeable coat is applied around the bilayers. The coated devices are dried in an air oven at 30. C to 50° C. for up to 18 hours. Finally, a 25 mil orifice exit is drilled through the semipermeable wall connecting the first composition with the exterior of the delivery device.

EXAMPLE 2

Following the procedure in Example 1, an osmotic dosage form is prepared comprising: a first composition consisting of 5.00 wt % bromocriptine mesylate, 70 wt % maltodextrin of 1800 molecular weight, 20 wt % hydroxypropylcellulose of 60,000 molecular weight, 4 wt % maleic acid and 1 wt % polyethylene glycol 30 castor oil; a second composition comprising 55 wt % sodium carboxy- methylcellulose with a molecular weight of approximately 700,000 grams per mole, 29 wt % sodium chloride, 14 wt % hydroxy- propylcellulose with a molecular weight of 60,000 grams per mole and 2 wt % ferric oxide; a wall comprising 95 wt % cellulose acetate having a 39.8% acetyl content and a molecular weight of approximately 40,000 grams per mole, and 5 wt % polyethylene glycol; and or 30 mil exit passageway. The device exhibits a release rate in mg per hour as seen in drawing FIG. 5 and the cumulative amount released is seen in drawing FIG. 6.

EXAMPLE 3

Following the procedure of Examples 1 and 2, an osmotic dosage form is manufactured wherein the first composition comprises an antiParkinson drug selected from the group consisting of bromocriptine; bromocriptine and its therapeutically acceptable salts; bromocriptine mesylate; ergot derivatives including lisuride, pergolide, and mesulergine; levodopa; carbidopa; levodopa-carbidopa; amantadine; deprenyl; trihexyphenidyl; benztropine; biperiden; ethopropazine; procyclidine; dopamine agonists; monamine oxidase inhibitors, antichlolinergics including benztropine mesylate, trihexyphenidyl hydrochloride, procyclidine hydrochloride, biperiden hydrochloride, and ethopropazine.

EXAMPLE 4

An osmotic device is manufactured as follows: first, a drug composition is prepared by adding 5 wt % deprenyl hydrochloride, 5 wt % hydroxypropylmethylcellulose, 30 wt % hydroxypropylcellulose, 60 wt % maltodextrin having a degree of polymerization of 7.4 and a molecular weight of 1200 to a blender and blending all of the ingredients for about 8 minutes. Then, while the ingredients are mixing, 60 ml of anhydrous ethanol is added slowly to the blender and the mixing continued for an additional 5 minutes. The wet granulation is passed through a 20 mesh screen, dried at room temperature for 16 hours and again passed through a 20 mesh screen. Finally, 1 wt % magnesium stearate pre-sifted through a 60 mesh screen is added to the granulation and all the ingredients mixed in a roller mill for 1 to 3 minutes.

Next, a second composition is prepared by mixing 30 wt % sodium carboxymethylcellulose, 18 wt % of polyethylene oxide with a molecular weight of approximately 5,000,000 grams per mole, 30 wt % of sorbitol, 20 wt % of hydroxypropylcellulose and 1 wt % of ferric oxide to a blender and all the ingredients mixed in a blender to produce a homogenous blend, which blend is passed through a 40 mesh screen. Next, 50 ml of anhydrous ethanol is added slowly to the blending mixture and all the ingredients mixed for an additional 5 minutes. The freshly prepared wet granulation is passed through a 30 mesh screen, allowed to dry at room temperature for 16 hours, and again passed through a 30 mesh screen. The screened granulation is mixed with 1 wt % of stearic acid in a roller mill for 1 minute.

A two-layered press is used for forming a bilaminated core. First the composition comprising the deprenyl drug is added to the press and tampered, then, the second composition is added to the press, and the two laminates pressed under a pressure of 1.8 tons into a contacting laminated arrangement.

Next, the laminate is surrounded with a semipermeable wall. The wall forming composition comprises 97 wt % cellulose acetate having an acetyl content of 39.8% and 3 wt % polyethylene glycol having a molecular weight of 400 grams per mole. The wall-forming composition is dissolved in acetone-water (95:5 wt:wt)

cosolvent to make a 4% solids solution. The wall-forming composition is sprayed onto and around the bilaminate in an Aeromatic Air ®Suspension Coater.

Finally, the wall coated bilaminates are dried for 24 hours at room temperature. Then, a 25 mil (0.635 mm) exit orifice is laser drilled on the drug side of the osmotic device. The residual solvent is removed by drying the osmotic device for 48 hours at 50° C. and 50% relative humidity. The osmotic devices are then dried for 1 hour at 50° C. to remove any excess moisture.

EXAMPLE 5

An osmotic dosage form is manufactured as follows: first, an anti-Parkinson drug pair comprising bromocriptine and deprenyl is made by adding 1700 ml of distilled water to a blender, to which is added 150 g of maltodextrin polymer having a degree of polymerization of 11.1 and a molecular weight of 1,800 and the stirring continued to produce a solution. Next, 50 g of bromocriptine mesylate and 60 g of deprenyl hydrochloride is added to the maltodextrin solution, and the mixing continued until all the ingredients comprising the first composition are blended with the solvent.

Next, 10 g of hydroxypropylcellulose having a molecular weight of 100,000 and 15 g of polyvinyl pyrrolidone are blended to provide a homogenous composition that is screened through a 40 mesh screen. The screened composition is added to a granulator column heated to 40° C. Then, the composition comprising the bromocriptine and the eldepryl and the polyvinyl pyrrolidone is sprayed on the column to produce a wet granulation. Next, the granulation is dried in the fluidizing air of the column for about 10 minutes while maintaining the column at 30° C. The granulation is removed from the column and screened through a 20 mesh screen. Next, 0.5 g of magnesium stearate is added to the granulation accompanied by 2 minutes of blending to yield the bidrug granulation.

Next, 700 ml of distilled water is added to a mixer, followed by 63 g of hydroxypropylcellulose having a 70,000 molecular weight with continual mixing to yield a solution. Then, 550 g of sodium chloride carboxymethylcellulose, 150 g of sodium chloride, 140 g of mannitol, and 70 g of hydroxypropylcellulose having a 60,000 molecular weight, and optionally 20 g of ferric oxide are blended into a homogenous blend, and then screened through a 40 mesh screen. The screened blend is added to the granulation solution in the granulator and it is sprayed onto the blend. Then, the granulation is dried in the fluidizing air for about 10 minutes, removed from the column and screened through a 20 mesh screen. Then, 3 g of magnesium stearate and 5 g of silicon dioxide are added to the granulation, the ingredients blended for 6 minutes and screened through a 80 mesh screen to yield the expandable composition.

The first composition and the second composition are arranged and pressed into bilayer cores by compressing 155 mg of the first composition and 95 mg of the second composition together under a force of 1.8 tons. The bilayers are coated with a coating solution comprising methylene chloride-methanol, cellulose triacetate and polyethylene glycol. The bilayers are coated in an air suspension coater with 500 g of the coating composition. The coated devices are dried in an air oven for 18 hours at 50° C. A 30 ml orifice is drilled through the semipermeable wall for connecting the drug composition with the exterior of the device.

EXAMPLE 6

A novel dosage form provided by the invention is manufactured as follows: first, 70 wt % of mannitol is put through a 40 mesh screen and then sieved through a 60 mesh screen, all the mannitol that went through the 60 mesh screen is used for preparing the dosage form. Next, 5 wt % eldepryl hydrochloride and 10 wt % carbidopalevodopa, 5 wt % microcrystalline cellulose, and 8 wt % of a maltodextrin comprising a molecular weight of 20,000 and a degree of polymerization of 123 independently are screened through a 40 mesh screen, and the screened ingredients mixed in a blender with the mannitol for about 20 minutes to produce a homogenous blend. Next, 1 wt % silicon dioxide is screened through an 80 mesh screen, and then 1 wt % magnesium is screened though an 80 mesh screen. The screened silicon dioxide and the screened magnesium stearate are added to the blend comprising the mannitol, eldepryl, carbidopa-levodopa, microcrystalline cellulose, and the maltodextrin polymer and blended for 5 minutes.

Next, 80 wt % of a copolymer of N-vinyl lactam and N-vinyl pyrrolidone, 13 wt % of sodium chloride, and 5 wt % of hydroxypropylmethylcellulose are wet granulated using ethyl alcohol as the granulating fluid. The wet granulation is screened through a 16 mesh screen and dried on trays at 50° C. in an oven overnight. The dried granulation is screened through a 16 mesh screen. Then a mixed lubricant comprising 1 wt % magnesium stearate and 1 wt % stearic acid is screened through a 80 mesh screen and added to the dried granulation. Finally, all the ingredients are blended for 5 minutes to yield a homogenous blend.

A dosage form comprising a first drug layer, and a hydrophilic layer is prepared in a Carver ®press using a ¼ inch, standard concave die. First, 86 mg of the composition comprising the drug layer is placed in the die and pinched to compress the granulation. The, the second-forming layer comprising the hydrophilic polymer is placed on top of the first layer and compressed with 2.5 tons of force.

The two-layered laminate is surround with a wall in an Aeromatic ®Coater. The wall-forming composition comprised 51 g of cellulose acetate having an acetyl content of 43.5%, 9 g of hydroxypropylcellulose, and a cosolvent comprising 1,170 ml of methylene chloride and 490 ml of methanol. During the wall-forming process, 960 ml of wall-forming solution are used to apply a 12.3 mg wall on each two-layered dosage form. The dosage forms are dried in an oven overnight at 50° C. to yield a final dry wall of 10.4 mg per dosage form. A single 15 mil, (0.381 mm) passageway is drilled through the wall connecting the exterior of the dosage form with the first layer. The first layer is selected by visual examination. In an automatic laser drilling technique, the drug layer is selected by the photo examination apparatus of the laser. The dosage form delivers 98.6% of its drugs in 24 hours.

EXAMPLE 7

The procedure of example 1 is repeated with the manufacturing steps as previously described, except that sodium chloride is replace by an osmotically effective solute selected from the group consisting of potassium chloride, magnesium chloride, d-mannitol and fructose.

EXAMPLE 8

An exterior, quick-releasing lamina comprising the drug pair bromocriptine mesylate and deprenyl hydrochloride and at least one quick-releasing member selected from the group consisting of hydroxypropylcellulose and hydroxypropylmethylcellulose are added to a fluid bed granulator and the materials blended in a moving current of air. Then, a granulating fluid is sprayed onto the fluidizing powers until the powders are wet granulated. Next, the fluidizing process is continued until the granulation is dry. The immediate release lamina is compressed or air sprayed around the external surface of the delivery device as prepared in the previous examples to yield an immediate release coat comprising the bromocriptine and the deprenyl.

DISCLOSURE OF METHOD OF PERFORMING THE INVENTION

An embodiment of the invention pertains to a method for delivering a beneficial drug at a controlled rate orally to a warm-blooded animal in need of drug therapy, which method comprises the steps of: (A) admitting into the warm-blooded animal a dosage form comprising: (1) a wall surrounding a compartment, the wall comprising at least in part a semipermeable polymeric composition permeable to the passage of fluid and substantially impermeable to the passage of drug; (2) a layer in the compartment comprising a formulation comprising a dosage unit amount of a drug for performing a therapeutic program and a maltodextrin; (3) a layer in the compartment comprising an osmotic formulation for imbibing, and absorbing fluid for expanding in size for pushing the drug maltodextrin formulation from the dosage form; and, (4) at least one IO passageway in the wall for releasing the drug; (B) imbibing fluid through the semipermeable part of the wall at a rate determined by the permeability of the semipermeable wall and the osmotic pressure gradient across the semipermeable wall causing the osmotic layer to expand and swell; and (C) delivering the beneficial drug from the dosage form through the exit passageway to the warm-blooded animal over a prolonged period of time. The method of the invention can be used for administering bromocriptine as a prolactin inhibitor.

Dosage form 10 of this invention, and as seen in the above drawing figures, can be used in a method for administering a drug by the oral route, and in another method the dosage form can be sized and shaped for administering a drug by the sublingual and buccal routes. The sublingual and buccal routes can be used for quicker therapy and they can be used when a smaller dose of drug is needed for therapy. The latter routes can be used as a by-pass of the first pass of hepatic metabolism of the drug. The sublingual or buccal routes can be used for administering a drug such as eldepryl, levodopa-carbidopa and the like, and for administering more than one drug such as eldepryl as an adjunct in the management of Parkinsonian patients being treated with levodopa-carbidopa, and the like.

In summary, it will appreciated that the present invention contributes to the art an unobvious dosage form that possesses practical utility, can administer a drug at a dose metered release rate per unit time. While the invention has been described and pointed out in detail with reference to operative embodiments thereof, it will be understood that those skilled in the art that various changes, modifications, substitutions and omissions can be made without departing from the spirit of the invention. It is intended, therefore, that the invention embraces those equivalents within the scope of the claims which follow.

We claim:

1. An improvement in a dosage form for delivering a drug to an animal, wherein the dosage form comprises:
   (a) a wall comprising a composition permeable at least in part to the passage of fluid, which wall surrounds;
   (b) a compartment;
   (c) at least one exit passageway in the wall that connects the exterior of the dosage form with the composition;
   (d) a composition in the compartment comprising a hydrogel that in the presence of fluid in the compartment expands and occupies space in the compartment; and,
   (e) a composition in the compartment comprising a and an osmotically effective solute, wherein the improvement comprises a maltodextrin in the composition that is compatible with the drug, aids in delivering the drug through the passageway from the compartment and comprises a 500 to 1,000,000 molecular weight and a degree of polymerization of 3 to 6,140.

2. The dosage form for delivering a drug according to claim 1, wherein the drug is a member selected from the group consisting of bromocriptine and its therapeutically acceptable salts.

3. The dosage form for delivering a drug according to claim 1, wherein the drug is a member selected from the group consisting of eldepryl and its therapeutically active salts.

4. The dosage form for drug according to claim 1, wherein the drug is a member selected from the group consisting of lisuride, pergolide, mesulergine, levodopa, carbidopa, levodopa-carbidopa, amantadine, trihexyphenidyl, benztropine, biperiden, ethopropazine, procyclidine, benztropine mesylate, trihexyphenidyl hydrochloride, procyclidine hydrochloride, and biperiden hydrochloride.

5. The dosage form for drug according to claim 1, wherein the drug is present in the composition as a drug pair, said pair comprising a member selected from the group consisting of bromocriptine, lisuride, pergolide, mesulergine, levodopa, carbidopa, levodopa-carbidopa, amantadine, deprenyl, trihexyphenidyl, benztropine, biperiden, ethopropazine, and procyclidine, and a different member selected from the group consisting of bromocriptine, lisuride, pergolide, mesulergine, levodopa, carbidopa, levodopacarbidopa, amantadine, deprenyl trihexyphenidyl, benztropine, biperiden, ethopropazine, and procyclidine.

6. An improvement in a method of drug therapy, wherein the method comprises:
   (A) admitting into a patient a dosage form, which dosage form comprises:
     (1) a wall comprising a composition that is permeable to the passage of fluid, which wall surrounds;
     (2) a compartment;
     (3) a composition in the compartment comprising a non-toxic hydrogel that imbibes fluid and expands in the presence of the imbibed fluid;
     (4) a passageway in the wall connecting the exterior of the dosage form with the compartment;
     (5) a composition in the compartment comprising a drug and wherein the improvement comprises a maltodextrin in the composition that is compatible with the drug for providing substantially complete delivery of the drug from the dosage form;

(B) imbibing fluid into the compartment for the hydrogel to absorb and expand thereby pushing the drug through the passageway; and (c) administering the drug to the patient in need of the drug.

7. An improvement in a method of drug therapy according to claim 6, wherein the drug is bromocriptine administered as a prolactin inhibitor.

* * * * *

UNITED STATES PATENT AND TRADEMARK OFFICE
CERTIFICATE OF CORRECTION

PATENT NO. : 5,057,321

DATED : October 15, 1991

INVENTOR(S) : David E. Edgren; Gurdish K. Bhatti; Howard A. Carpenter

It is certified that error appears in the above-identified patent and that said Letters Patent is hereby corrected as shown below:

In claim 1, column 16, line 19, following the word "composition" delete "a".

In claim 1, column 16, line 20, delete "and".

In claim 5, column 16, line 52, "levodopacarbidopa," should read ----levodopa-carbidopa,----.

Signed and Sealed this

Sixteenth Day of March, 1993

Attest:

STEPHEN G. KUNIN

*Attesting Officer*  Acting Commissioner of Patents and Trademarks